United States Patent
Noguchi et al.

(10) Patent No.: US 11,065,070 B2
(45) Date of Patent: Jul. 20, 2021

(54) ROBOT SYSTEM AND METHOD OF OPERATING THE SAME

(71) Applicant: KAWASAKI JUKOGYO KABUSHIKI KAISHA, Kobe (JP)

(72) Inventors: Kenji Noguchi, Kobe (JP); Masayuki Kamon, Akashi (JP); Shigetsugu Tanaka, Akashi (JP)

(73) Assignee: KAWASAKI JUKOGYO KABUSHIKI KAISHA, Kobe (JP)

(*) Notice: Subject to any disclaimer, the term of this patent is extended or adjusted under 35 U.S.C. 154(b) by 219 days.

(21) Appl. No.: 15/755,111

(22) PCT Filed: Jul. 15, 2016

(86) PCT No.: PCT/JP2016/003356
§ 371 (c)(1),
(2) Date: Feb. 26, 2018

(87) PCT Pub. No.: WO2017/033391
PCT Pub. Date: Mar. 2, 2017

(65) Prior Publication Data
US 2018/0243918 A1  Aug. 30, 2018

(30) Foreign Application Priority Data

Aug. 25, 2015 (JP) .............................. JP2015-165479

(51) Int. Cl.
*G05B 15/00* (2006.01)
*G05B 19/00* (2006.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ......... A61B 34/37; A61B 34/32; A61B 34/70; A61B 34/35; G05B 19/4182;
(Continued)

(56) References Cited

U.S. PATENT DOCUMENTS 6,070,109 A * 5/2000 McGee .................. B25J 9/1692
700/254
6,522,949 B1   2/2003 Ikeda et al.
(Continued)

FOREIGN PATENT DOCUMENTS

CN        1319478 A    10/2001
CN      101314224 A    12/2008
(Continued)

OTHER PUBLICATIONS

Feb. 27, 2018 International Preliminary Report on Patentability issued in International Patent Application No. PCT/JP2016/003356.
(Continued)

*Primary Examiner* — Harry Y Oh
*Assistant Examiner* — Sohana Tanju Khayer
(74) *Attorney, Agent, or Firm* — Oliff PLC

(57) ABSTRACT

A robot system which includes a manipulator configured to receive a manipulating instruction from an operator, a slave arm having a plurality of joints, and a control device configured to control operation of the slave arm. The control device is configured, while the slave arm is operating at a speed equal to or higher than a first given the threshold, even when an operational instruction value for correcting the operation of the slave arm is inputted from the manipulator
(Continued)

during an automatic operation of the slave arm, to prevent the correction of the operation of the slave arm.

6 Claims, 6 Drawing Sheets

(51) Int. Cl.
*A61B 34/37* (2016.01)
*G05B 19/418* (2006.01)
*B25J 9/00* (2006.01)
*B25J 9/16* (2006.01)
*B23P 19/04* (2006.01)
*B25J 13/00* (2006.01)
*B25J 19/04* (2006.01)
*B25J 13/08* (2006.01)
*B25J 3/00* (2006.01)
*B25J 13/06* (2006.01)
*B25J 18/00* (2006.01)
*B25J 19/02* (2006.01)
*B25J 3/04* (2006.01)
*B23Q 15/12* (2006.01)
*B25J 13/02* (2006.01)
*B25J 11/00* (2006.01)
*G06F 3/01* (2006.01)
*H04N 5/232* (2006.01)
*H04N 7/18* (2006.01)
*A61B 34/32* (2016.01)
*G06T 7/62* (2017.01)
*G06T 7/70* (2017.01)
*B23P 21/00* (2006.01)

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC .......... G05B 2219/40195; G05B 2219/40134; G05B 2219/40183; G05B 2219/40627; G05B 2219/40146; G05B 2219/40161; G05B 2219/39102; G05B 2219/37297; G05B 2219/40136; G05B 2219/40162; G05B 2219/40139; G05B 2219/40387; G05B 2219/40145; G05B 2219/40182; G05B 2219/39004; G05B 2219/40143; G05B 2219/40169; G05B 2219/33007; G05B 2219/40142; G05B 2219/35464; G05B 2219/39533; G05B 2219/40163; G05B 2219/39531; G05B 2219/40022; G05B 2219/39439; B25J 9/1646; B25J 9/0081; B25J 9/1653; B25J 13/084; B25J 9/1682; B25J 9/1664; B25J 9/161; B25J 18/00; B25J 13/088; B25J 13/087; B25J 13/085; B25J 9/1602; B25J 19/028; B25J 9/1612; B25J 9/1674; B25J 13/025; B25J 13/065; B25J 13/003; B25J 9/1633; B25J 3/04; B25J 19/023; B25J 9/1689; B25J 11/008; B25J 9/163; B25J 13/02; B25J 9/1628; B25J 9/126; B25J 19/06; B25J 19/02; B25J 11/005; B25J 9/1692; B25J 9/1661; B25J 13/06; B25J 9/1669; B25J 3/00; B25J 9/0087; B25J 13/08; B25J 13/006; B25J 9/1697; B25J 9/0084; B25J 19/04; B25J 13/00; G06T 7/70; G06T 7/62; H04N 7/181; H04N 5/23219; B23P 21/002; B23P 21/00; B23P 19/04; Y10S 901/02; Y10S 901/03; Y10S 901/08; Y10S 901/47; Y10S 901/09; Y10S 901/46; Y10S 901/10; Y10S 901/41; Y10S 901/27; G06F 3/017; B23Q 15/12
See application file for complete search history.

(56) References Cited

U.S. PATENT DOCUMENTS 9,167,418 B1 * 10/2015 Tuluca .............. H04M 1/72577
2002/0103575 A1    8/2002 Sugawara
2008/0022790 A1 *  1/2008 Lee .................. G01C 19/42
                                                    74/5.4
2008/0297092 A1   12/2008 Nihei et al.
2010/0161129 A1 *  6/2010 Costa ................. A61B 34/30
                                                    700/259
2011/0208355 A1    8/2011 Tsusaka
2012/0277912 A1   11/2012 Kirihara

(56) References Cited

U.S. PATENT DOCUMENTS

| | | | |
|---|---|---|---|
| 2014/0067128 A1* | 3/2014 | Kowalski | G05B 19/409 |
| | | | 700/264 |
| 2016/0016313 A1* | 1/2016 | Oyama | B25J 9/1674 |
| | | | 700/253 |
| 2016/0229052 A1* | 8/2016 | Touma | B25J 9/161 |
| 2018/0257226 A1* | 9/2018 | Civette | B25J 9/1664 |

FOREIGN PATENT DOCUMENTS

| | | | |
|---|---|---|---|
| CN | 102300679 A | 12/2011 | |
| CN | 102756374 A | 10/2012 | |
| EP | 1 138 448 A2 | 10/2001 | |
| JP | 2001-088071 A | 4/2001 | |
| JP | 2002-304205 A | 10/2002 | |
| JP | 2003-311661 A | 11/2003 | |
| JP | 2013-071231 A | 4/2013 | |
| JP | 2016-083713 A | 5/2016 | |

OTHER PUBLICATIONS

Sep. 27, 2016 International Search Report issued in International Patent Application No. PCT/JP2016/003356.

\* cited by examiner

ROBOT SYSTEM AND METHOD OF OPERATING THE SAME

TECHNICAL FIELD

The present disclosure relates to a robot system and a method of operating the same.

BACKGROUND ART

Conventionally, an iterative work, such as welding, painting, assembling of components, and application of seal adhesive, is automatically performed in a manufacture site by an industrial robot. In order to make the robot to perform the work, the robot is necessary to be taught with information required for the work and store the information therein.

A method of teaching the robot includes, for example, teaching by a remote control using a teaching pendant (e.g., Patent Document 1). Additionally, it is known to perform direct teaching for teaching by storing a route of work in a robot arm (e.g., Patent Document 2).

REFERENCE DOCUMENTS OF CONVENTIONAL ART

Patent Documents

[Patent Document 1] JP2016-083713A
[Patent Document 2] JP2013-071231A

DESCRIPTION OF THE DISCLOSURE

Problems to be Solved by the Disclosure

Meanwhile, part of the operation taught to the robot may be necessary to be changed for various reasons, for example, a case where, after finishing the teaching, a fault is discovered in the initially-created teaching information for part of the work.

In such a case, the teaching information to be used for an automatic operation of the robot is changed by again performing the teaching. However, if the operation of the robot is to be corrected while an operating speed of the robot under the automatic operation is high, the operation of the robot is corrected sharply and the robot may operate in an unexpected direction.

Therefore, the present disclosure is to provide a robot system and a method of operating the same, which are capable of preventing that, when correcting operation of a robot during an automatic operation, the operation of the robot is corrected sharply and the robot operates in an unexpected direction.

SUMMARY OF THE DISCLOSURE

In order to solve the conventional issue, a robot system according to the present disclosure includes a manipulator configured to receive a manipulating instruction from an operator, a slave arm having a plurality of joints, and a control device configured to control operation of the slave arm. The control device is configured, while the slave arm is operating at a speed equal to or higher than a first given preset threshold, even when an operational instruction value for correcting the operation of the slave arm is inputted from the manipulator during an automatic operation of the slave arm, to prevent the correction of the operation of the slave arm.

Thus, it is possible to prevent that, when correcting operation of a robot (slave arm) during the automatic operation, the operation of the robot is corrected sharply and the robot operates in an unexpected direction.

Further, a method of operating a robot system according to the present disclosure is a method of operating a robot system including a manipulator configured to receive a manipulating instruction from an operator, and a slave arm having a plurality of joints. The method includes (A) causing the manipulator to output an operational instruction value for correcting operation of the slave arm when the slave arm is under an automatic operation, and (B) preventing the correction of the operation of the slave arm when the slave arm is operating at a speed equal to or higher than a first given preset threshold.

Thus, it is possible to prevent that, when correcting operation of the robot during the automatic operation, the operation of the robot is corrected sharply and the robot operates in the unexpected direction.

Effect of the Disclosure

According to the robot system and the method of operating the same of the present disclosure, it is possible to prevent that when correcting operation of the robot during the automatic operation, the operation of the robot is sharply corrected and the robot is operated in the unexpected direction.

MODES FOR CARRYING OUT THE DISCLOSURE

Figure 1:
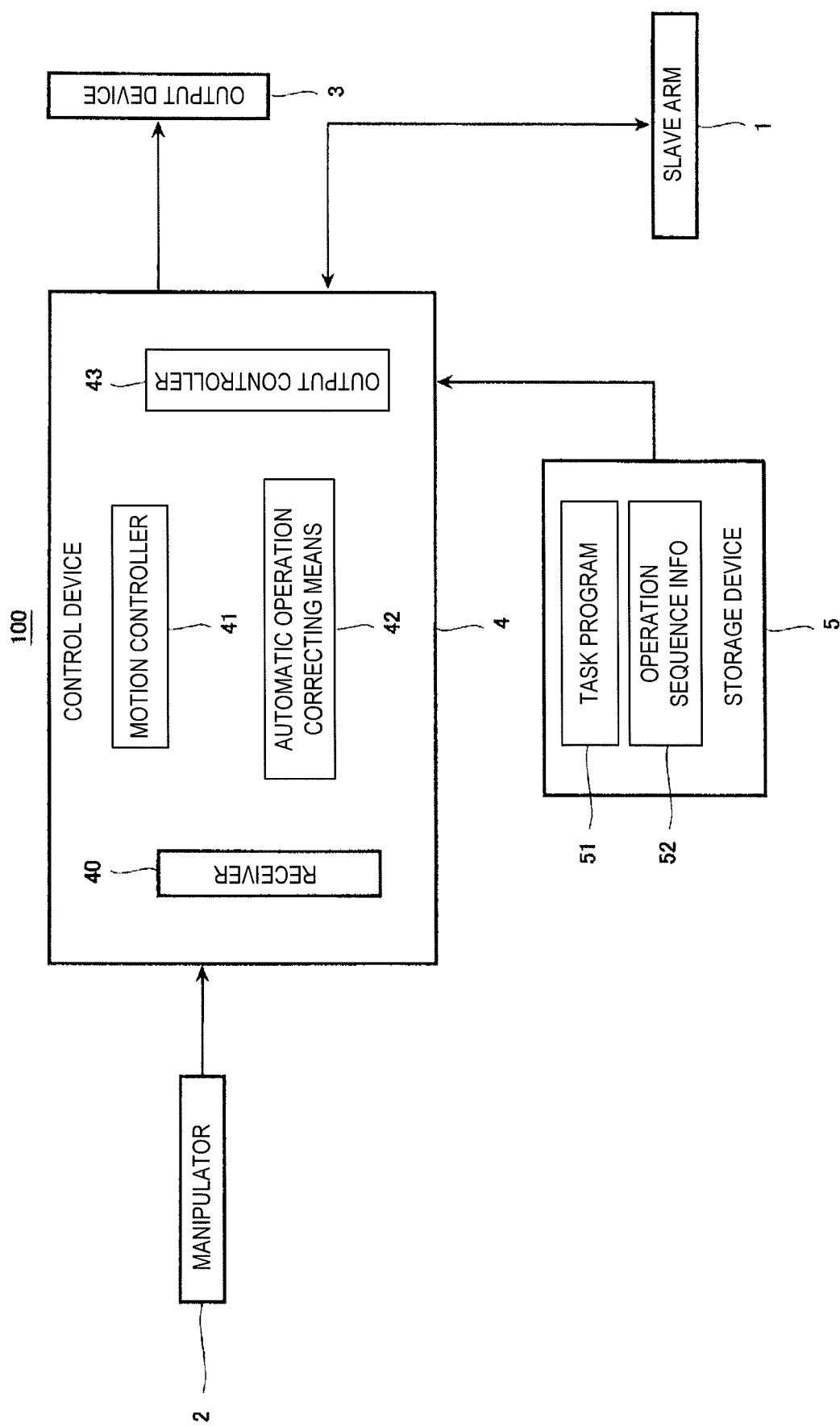
FIG. 1 is a block diagram illustrating a schematic configuration of a robot system according to a first embodiment.

Hereinafter, embodiments of the present disclosure will be described with reference to the drawings. Note that, throughout the drawings, the same reference characters are assigned to the same or corresponding parts and redundant description is omitted. Further, throughout the drawings, components for describing the present disclosure are selectively illustrated and illustration of the other components may be omitted. Furthermore, the present disclosure is not limited to the following embodiments.

First Embodiment

A robot system according to the first embodiment includes a manipulator which receives a manipulating instruction from an operator, a slave arm having a plurality of joints, and a control device which controls operation of the slave arm. The control device is configured, while the slave arm is operating at a speed equal to or higher than a first given preset threshold, even when an operational instruction value for correcting the operation of the slave arm is inputted from the manipulator during an automatic operation of the slave arm, to prevent the correction of the operation of the slave arm.

Further the robot system according to the first embodiment may further include an output device. The control device may be configured, when the operational instruction value for correcting the operation of the slave arm is inputted from the manipulator while the slave arm is operating at a speed equal to or higher than the first threshold during the automatic operation of the slave arm, to cause the output device to output correction preventing information indicating that the correction of the operation of the slave arm is prevented.

Hereinafter, one example of the robot system according to the first embodiment is described with reference to FIGS. 1 to 5.

[Configuration of Robot System]

Figure 2:
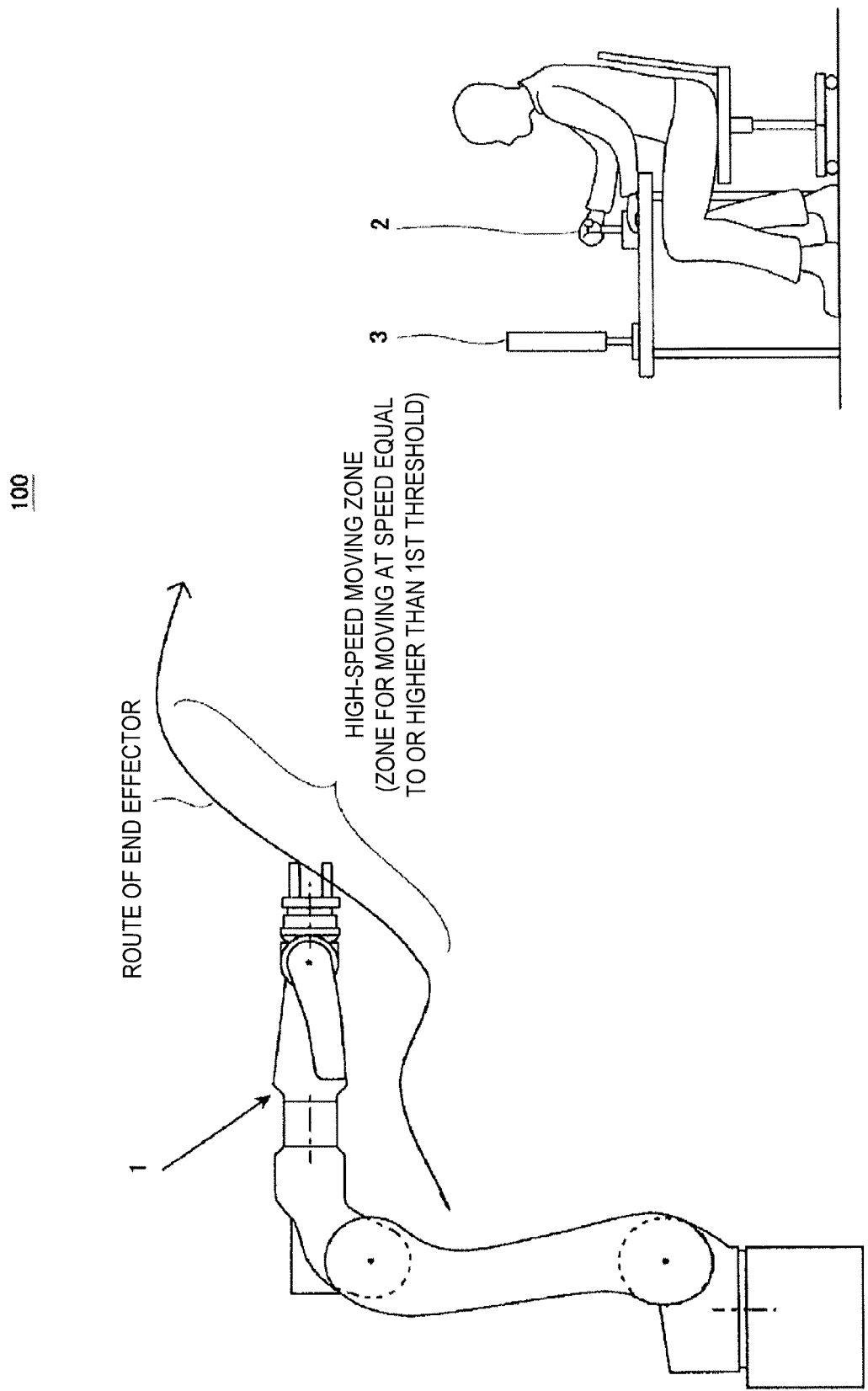
FIG. 2 is a schematic diagram illustrating a schematic configuration of the robot system according to the first embodiment.

FIG. 1 is a block diagram illustrating a schematic configuration of the robot system according to the first embodiment. FIG. 2 is a schematic diagram illustrating a schematic configuration of the robot system according to the first embodiment.

As illustrated in FIGS. 1 and 2, the robot system 100 according to the first embodiment includes a slave arm 1, a manipulator 2, an output device 3, a control device 4 and a storage device 5. The control device 4 is configured, while the slave arm 1 is operating at a speed equal to or higher than a first given preset threshold, even when an operational instruction value for correcting the operation of the slave arm 1 is inputted from the manipulator 2 during an automatic operation of the slave arm 1, to prevent the correction of the operation of the slave arm 1.

Here, in this specification, the control mode in which the salve arm 1 operates according to a preset task program is referred to as "automatic operation mode." In the automatic operation mode, similar to a conventional teaching playback robot, the slave arm 1 automatically performs a given work without the operator manipulating the manipulator 2.

Moreover, in this specification, the control mode in which the slave arm 1 operates based on the operation of the operator received by the manipulator 2 is referred to as "manual operation mode." Note that, in the manual operation mode, the slave arm 1 may be operated to completely follow a manipulating instruction received from the manipulator 2, or the slave arm 1 may be operated while correcting the manipulating instruction received from the manipulator 2 with a preset program (e.g., hand shake correction).

Furthermore, in this specification, the control mode in which the slave arm 1 operates according to the preset task program is corrected by the operator's manipulation received by the manipulator 2 is referred to as "automatic operation correcting mode."

Hereinafter, respective devices constituting the robot system 100 according to the first embodiment are described in detail.

The slave arm 1 is a robot which is installed in a workspace and performs a series of works comprised of a plurality of processes. Note that the series of works comprised of the plurality of processes may include works, such as assembling of component(s) to a product and painting.

The slave arm 1 according to the first embodiment is an articulated robot, in a line production or a cell production, which is utilized at a production plant where products are produced by assembling electric and/or electronic components etc., is disposed along a workbench provided to the production plant, and is capable of performing at least one of works, such as transferring, assembling or relocating of component(s), and converting the posture, to workpiece(s) on the workbench. Note that the embodiment of the slave arm 1 is not limited to the configuration described above, but may be widely applied to any articulated robots, regardless of a horizontal articulated type or a vertical articulated type.

Here, a specific configuration of the slave arm 1 will be described with reference to FIG. 3.

Figure 3:
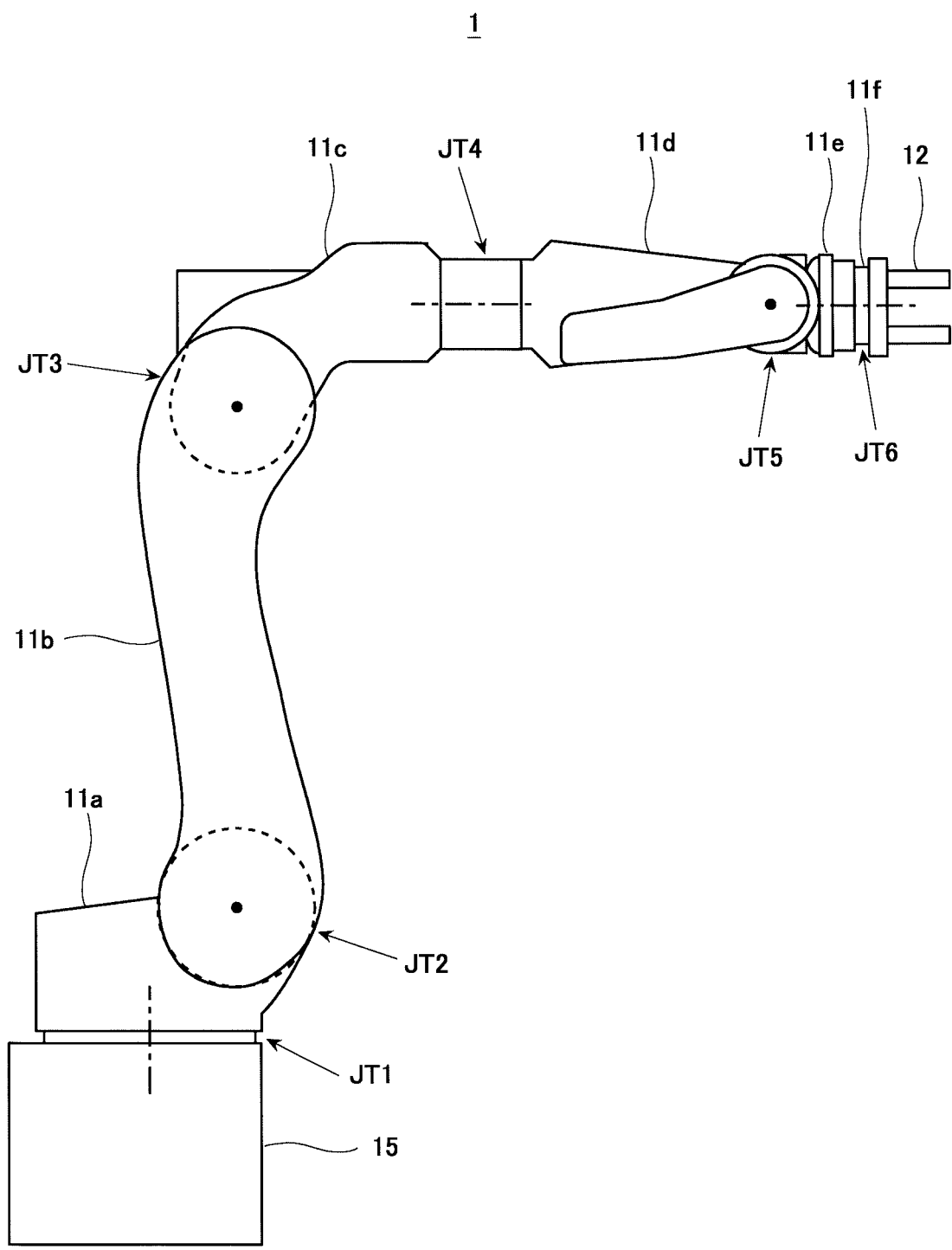
FIG. 3 is a schematic diagram illustrating a schematic configuration of a slave arm illustrated in FIGS. 1 and 2.

FIG. 3 is a schematic diagram illustrating a schematic configuration of a slave arm illustrated in FIGS. 1 and 2.

As illustrated in FIG. 3, the slave arm 1 is an articulated robot arm having a coupled body of a plurality of links (here, a first link 11a to a sixth link 11f), a plurality of joints (here, a first joint JT1 to a sixth joint JT6), and a pedestal 15 supporting them.

At the first joint JT1, the pedestal 15 and a base-end part of the first link 11a are coupled to each other so as to be rotatable about an axis extending vertically. At the second joint JT2, a tip-end part of the first link 11a and a base-end part of the second link 11b are coupled to each other so as to be rotatable about an axis extending horizontally. At the third joint JT3, a tip-end part of the second link 11b and a base-end part of the third link 11c are coupled to each other so as to be rotatable about an axis extending horizontally.

Further, at the fourth joint JT4, a tip-end part of the third link 11c and a base-end part of the fourth link 11d are coupled to each other so as to be rotatable about an axis extending in the longitudinal directions of the fourth link 11d. At the fifth joint JT5, a tip-end part of the fourth link 11d and a base-end part of the fifth link 11e are coupled to each other so as to be rotatable about an axis perpendicular to the longitudinal directions of the fourth link 11d. At the sixth joint JT6, a tip-end part of the fifth link 11e and a base-end part of the sixth link 11f are twistably and rotatably coupled to each other.

A mechanical interface is provided at a tip-end part of the sixth link 11f. Detachably attached to this mechanical interface is an end effector 12 corresponding to the contents of work.

Further, the first joint JT1 to the sixth joint JT6 are provided with drive motors M1-M6 as an example of actuators for relatively rotating two members to which each joint is connected, respectively. The drive motors M1-M6 may be, for example, servo motors which are servo-controlled by the control device 4. Moreover, the first joint JT1 to the sixth joint JT6 are provided with rotation sensors E1-E6 which detect rotational positions of the drive motors M1-M6 (see FIG. 5), and current sensors C1-C6 which detect currents for controlling the rotations of the drive motors M1-M6 (see FIG. 5), respectively. The rotation sensors E1-E6 may be, for example, encoders. Note that the description of the drive motors M1-M6, the rotation sensors E1-E6, and the current sensors C1-C6 described above are denoted by attaching the suffix of 1-6 to the alphabet corresponding to each of the joints JT1-JT6. Hereinafter, when an arbitrary joint is illustrated among the joints JT1-JT6, the joint is referred to as "joint JT" while omitting the suffix, and the same is applied to the drive motor M, the rotation sensor E, and the current sensor C.

The manipulator 2 is a device for receiving the manipulating instruction from the operator. Further, when operating the slave arm 1 in the manual operation mode or the automatic operation correcting mode, the manipulator 2 outputs to the control device 4 operation instruction values, such as positional information, attitude information, moving direction, moving speed of the slave arm 1, etc. by the operator's manipulation. The manipulator 2 may be, for example, a master arm, a joystick, or a tablet computer. Note that the manipulator 2 may be separately provided with an input part which inputs a start instruction of work, a notice of completion of the work by a manual operation etc., an adjuster (not illustrated) which adjusts a second coefficient B (see FIG. 5) etc. The adjuster may include, for example, a volume knob.

The output device 3 may include a display device, such as a monitor, a speaker, etc. For example, when the output device 3 is constituted by the display device, it displays (outputs) the information transmitted from the control device 4 as an image, for example, letter(s), a painting, a picture, a video, etc. When the output device 3 is constituted by the speaker, it outputs the information transmitted from the control device 4 as sound information. Note that when the manipulator 2 is constituted by a tablet computer, the output device 3 may be the tablet computer.

The storage device 5 is a readable and writable recording medium, which stores a task program 51 and operation sequence information 52 of the robot system 100. Note that, although in the robot system 100 according to the first embodiment, the storage device 5 is provided separately from the control device 4, it may be integrally provided with the control device 4.

The task program 51 is created by, for example, teaching by the operator using a teaching pendant etc., and stored in the storage device 5 in association with identification information on the slave arm 1 and the task. Note that the task program 51 may be created as an operation flow for each work.

The operation sequence information 52 is information regarding an operation sequence which defines a series of work processes performed by the slave arm 1 in the workspace. In the operation sequence information 52, an operation order of the work process and the control mode of the slave arm 1 are associated with each other. Further, in the operation sequence information 52, the task program for causing the slave arm 1 to automatically perform the work is associated with each work process. Note that the operation sequence information 52 may include a program for causing the slave arm 1 to automatically perform the work for each work process.

The control device 4 controls the operation of the slave arm 1, and includes a receiver 40, a motion controller 41, an automatic operation correcting means 42, and an output controller 43 as functional blocks. The control device 4 may be comprised of, for example, an arithmetic part (not illustrated), such as a microcontroller, an MPU and a PLC (Programmable Logic Controller), a logic circuit, etc., and a memory part (not illustrated), such as a ROM or a RAM. Moreover, each functional block provided to the control device 4 is implementable by the arithmetic part of the control device 4 reading and executing the program stored in a memory part or the storage device 5.

Note that the control device 4 may not only be in a form comprised of a single control device, but also in a form comprised of a group of control devices in which a plurality of control devices collaborate with each other to execute the control of the slave arm 1 (robot system 100).

The receiver 40 receives an input signal transmitted from the outside of the control device 4 and, for example, transmits an output signal from the control device 4 to the slave arm 1 etc. The input signal received by the receiver 40 may be, for example, a signal transmitted from the manipulator 2, a signal transmitted from a manipulating instruction part (not illustrated) other than the manipulator 2, or a position signal of the slave arm 1 transmitted from the rotation sensor E of the slave arm 1 described later (positional information), etc.

When the motion controller 41 receives a manipulating instruction from the manipulator 2 as the input signal, it determines the operating mode of the process which the slave arm 1 carries out in the series of works by using the manipulating instruction as a trigger. The motion controller 41 is capable of performing the determination of the operating mode of the process which the slave arm 1 carries out next, with reference to the operation sequence information 52 stored in the storage device 5. Once the motion controller 41 determines the operating mode, it controls the slave arm 1 so that the slave arm 1 is operated in the determined operating mode.

For example, if the motion controller 41 determines that the slave arm 1 is to be operated in the automatic operation mode, it controls the slave arm 1 to perform operation defined by the task program 51 or, by reading the operation sequence information 52, operation defined by a program contained in the operation sequence information 52.

Further, if the motion controller 41 determines that the slave arm 1 is to be operated in the manual operation mode, it controls the slave arm 1 to perform the operation based on the manipulating instruction received from the manipulator 2 by the receiver 40.

Further, if the motion controller 41 determines that the slave arm 1 is to be operated in the automatic operation correcting mode, it performs the operation defined by the task program 51 or, by reading the operation sequence information 52, the operation defined by the program contained in the operation sequence information 52, and when the receiver 40 receives a correction instructing signal as the input signal from the manipulator 2 during the operation of the slave arm 1 by the automatic operation mode, the operation of the slave arm 1 by the automatic operation is corrected to operation following the correction instructing signal from the manipulator 2.

Then, when the output of the correction instructing signal from the manipulator 2 is stopped and the receiver 40 stops receiving the correction instructing signal, or when the receiver 40 receives an instruction for resuming the automatic operation of the slave arm 1 from the manipulator 2, the motion controller 41 resumes the automatic operation of the slave arm 1.

When the receiver 40 receives the correction instructing signal (operational instruction value; correction instruction value) during the automatic operation of the slave arm 1, the automatic operation correcting means 42 instructs the motion controller 41 to correct the operation of the slave arm 1. Note that a specific method of correcting the operation of the slave arm 1 will be described later.

The output controller 43 controls the output device 3 to output information to be notified to the operator etc. as video information, image information or audio information. Specifically, for example, the output controller 43 controls the output device 3 to output correction preventing information outputted from the motion controller 41 and indicating that the correction of the operation of the slave arm 1 is prevented.

[Operation and Effect of Robot System]

Next, operation and effect of the robot system 100 according to the first embodiment are described with reference to FIGS. 1 to 5. Note that since the operation of performing the series of works by the operator manipulating the manipulator 2 to operate the slave arm 1 is executed similar to a known robot system, detailed description thereof is omitted.

Moreover, the following operation is executed by the arithmetic part of the control device 4 reading the program stored in the memory part of the control device 4 or the storage device 5.

Figure 4:
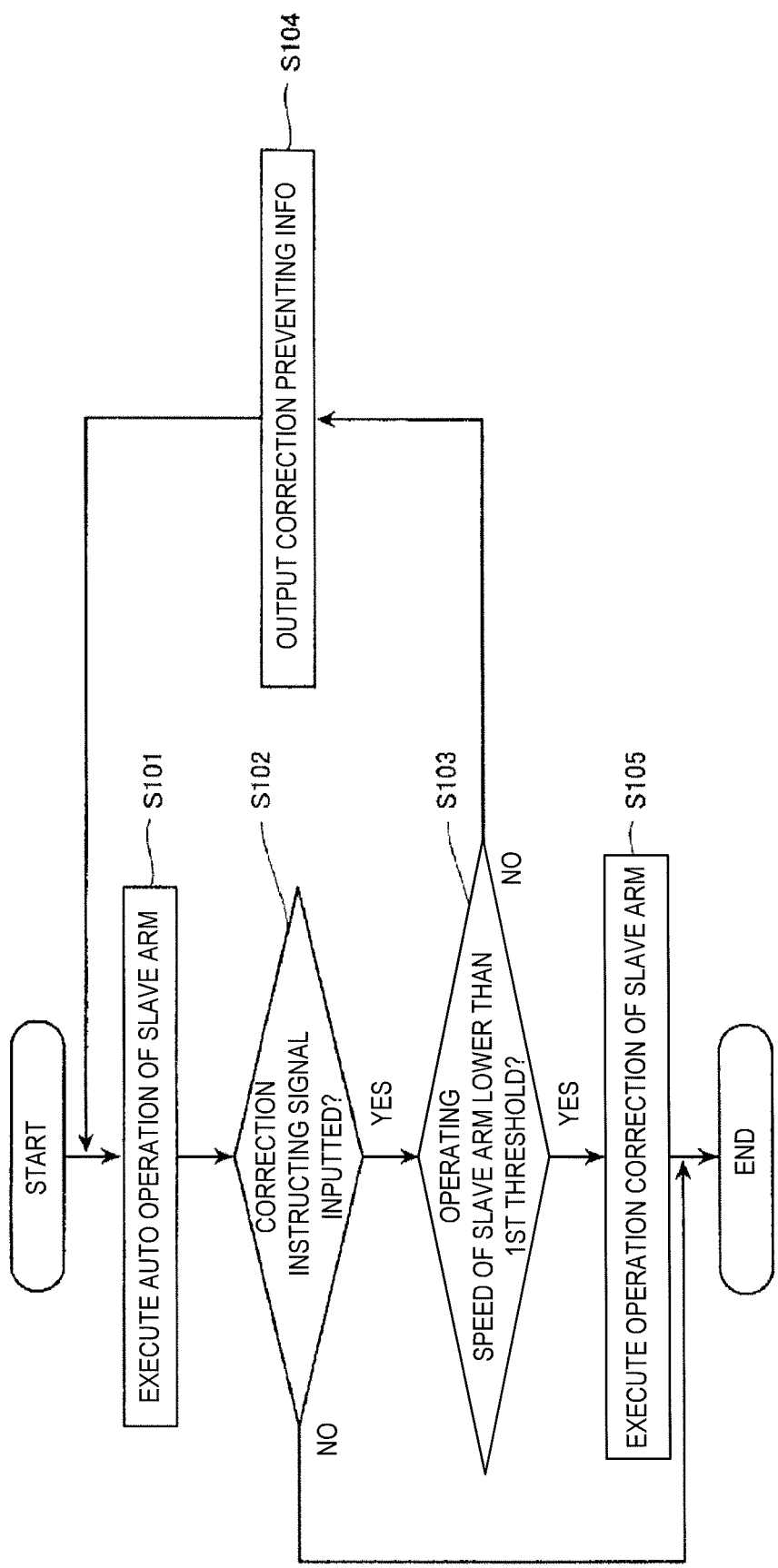
FIG. 4 is a flowchart illustrating one example of operation of the robot system according to the first embodiment.

FIG. 4 is a flowchart illustrating one example of operation of the robot system according to the first embodiment.

As illustrated in FIG. 4, while the slave arm 1 is operated in the automatic operation mode (Step S101), the motion controller 41 of the control device 4 determines whether the correction instructing signal is inputted to the receiver 40 from the manipulator 2 (Step S102).

If the motion controller 41 of the control device 4 determines that the correction instructing signal is not inputted from the manipulator 2 (NO at Step S102), it ends this program. Note that, when the control device 4 ends this program, it again executes this program, for example, after 50 msec. On the other hand, if the motion controller 41 of the control device 4 determines that the correction instructing signal is inputted (YES at Step S102), it executes processing illustrated at Step S103.

At Step S103, the motion controller 41 of the control device 4 determines whether the operating speed of the slave arm 1 is lower than the first preset threshold. Here, the first threshold is set in advance by experiment etc., and is a speed at which, if the operation of the slave arm 1 is corrected by the manipulator 2 while the slave arm 1 is operated in the automatic operation mode, the operation of the slave arm 1 may be sharply corrected and operate in an unexpected direction.

The first threshold may be, for example, 25 to 35% of a highest speed (°/sec) of each joint of the slave arm 1, or 25 to 35% of a highest speed (mm/sec) of the moving speed of the slave arm 1 when the slave arm 1 moves a workpiece (the moving speed of the end effector 12 or the workpiece). Further, when the slave arm 1 moves the workpiece linearly or curvedly, for example, the moving speed of the slave arm 1 (the moving speed of the end effector 12 or the workpiece) may be 250-350 mm/sec as the first threshold.

If the operating speed of the slave arm 1 is equal to or higher than the first threshold (NO at Step S103; for example, the end effector 12 of the slave arm 1 is located in a high-speed moving zone illustrated in FIG. 2), the motion controller 41 causes the output device 3 to output the correction preventing information via the output controller 43 (Step S104), and the automatic operation mode continues (Step S101). Note that the output of the correction preventing information may be performed by outputting (displaying) on the monitor etc. letter/character information, such as "the operating speed of the slave arm 1 is excessively high and not correctable" or by outputting the letter/character information as audio information from the speaker etc.

On the other hand, if when the operating speed of the slave arm 1 is lower than the first threshold (YES at Step S103), based on the correction instruction signal inputted from the manipulator 2 at Step S102, the motion controller 41 of the control device 4 performs the operation correction of the slave arm 1 (Step S105) and ends this program.

Next, the flow of signals when performing the operation correction of the slave arm 1 (Step S105 illustrated in FIG. 4) will be described with reference to FIG. 5.

Figure 5:
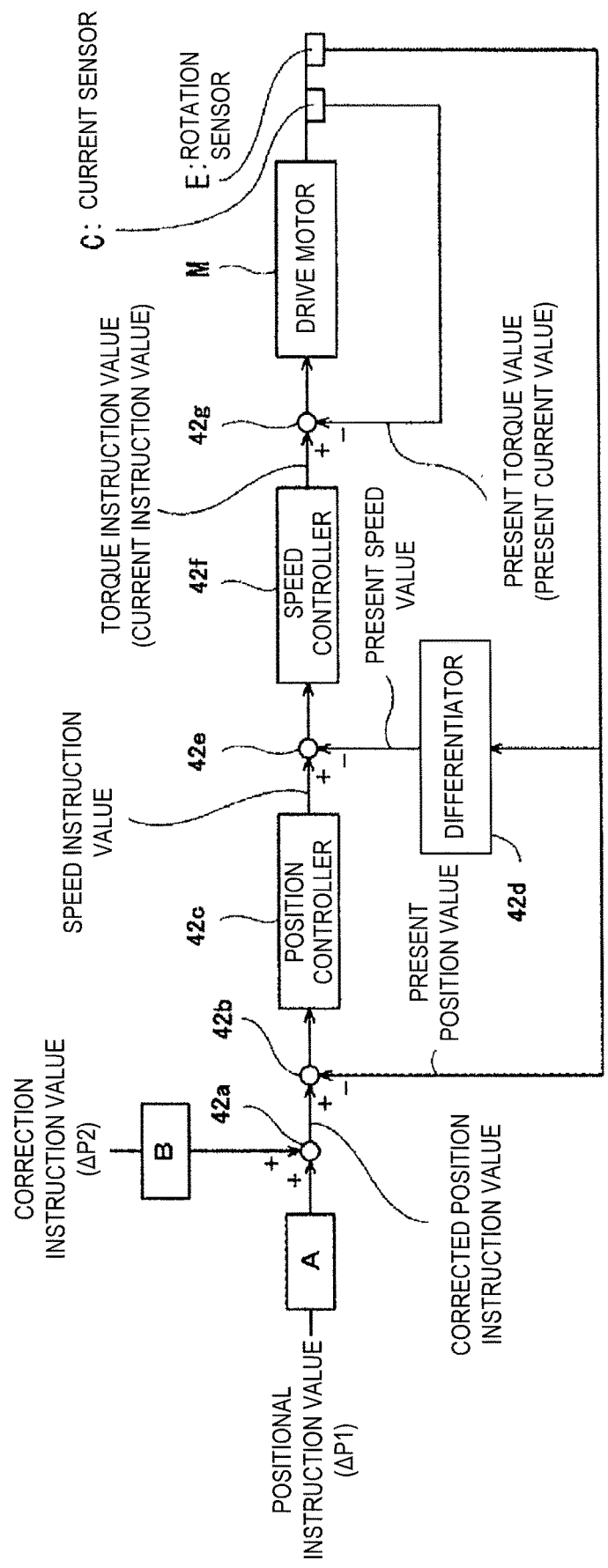
FIG. 5 is a block diagram illustrating one example of a control system of an automatic operation correcting means illustrated in FIG. 1.

FIG. 5 is a block diagram illustrating one example of a control system of the automatic operation correcting means illustrated in FIG. 1.

As illustrated in FIG. 5, the automatic operation correcting means 42 includes an adder 42a, subtractors 42b, 42e and 42g, a position controller 42c, a differentiator 42d, and a speed controller 42f, and controls the rotational position of the drive motor M of the slave arm 1 in response to the instruction value which is based on the automatic operation information acquired from the task program 51 (operational instruction value ΔP1) and the instruction value which is based on the manipulation information inputted from the manipulator 2 (correction instruction value ΔP2). Note that the operational instruction value ΔP1 and the correction instruction value ΔP2 here are the positional information (position coordinate information).

The adder 42a adds the correction instruction value ΔP2 to the operational instruction value ΔP1 to generate a corrected position instruction value. Here, the adder 42a generates the position instruction value according to the following Equation (1).

$$\Delta P0 = A \times \Delta P1 + B \times \Delta P2 \qquad \text{Equation (1)}$$

Here, a first coefficient A and a second coefficient B are variables, and they are in a relationship in which when one of the coefficients increases, the other coefficient decreases. More specifically, the first coefficient A and the second coefficient B may be coefficients with which a value obtained by multiplying the first coefficient A and the second coefficient B becomes a given preset first value, or coefficients with which a value obtained by adding the first coefficient A and the second coefficient B becomes a given preset second value. Note that the first given value or the second given value may be 1, 10 or 100.

The subtractor 42b subtracts a present position value detected by the rotation sensor E from the corrected position instruction value to generate an angle deviation. The subtractor 42b outputs the generated angle deviation to the position controller 42c.

The position controller 42c generates a speed instruction value from the angular deviation inputted from the subtractor 42b by arithmetic processing based on a predetermined transfer function or proportional coefficient. The position controller 42c outputs the generated speed instruction value to the subtractor 42e.

The differentiator 42d differentiates the present position value information detected by the rotation sensor E to generate a change amount of the rotation angle of the drive motor M per unit time, that is, the present speed value. The differentiator 42d outputs the generated present speed value to the subtractor 42e.

The subtractor 42e subtracts the present speed value inputted from the differentiator 42d from the speed instruction value inputted from the position controller 42c to generate a speed deviation. The subtractor 42e outputs the generated speed deviation to the speed controller 42f.

The speed controller 42f generates a torque instruction value (current instruction value) from the speed deviation inputted from the subtractor 42e by arithmetic processing based on a predetermined transfer function or proportional coefficient. The speed controller 42f outputs the generated torque instruction value to the subtractor 42g.

The subtractor 42g subtracts a present current value detected by the current sensor C from the torque instruction value inputted from the speed controller 42f to generate a current deviation. The subtractor 42g outputs the generated current deviation to the drive motor M to drive the drive motor M.

Note that, as described above, the second coefficient B may be inputted to the automatic operation correcting means 42 by the operator manually adjusting the adjuster provided to the manipulator 2. Further, as the adjuster, for example, a program for causing the second coefficient B to be 0 at a great distance from the work target (a structure to which a workpiece is attached, etc.), and to be gradually increased as approaching the work target may be stored in advance in the storage device 5.

Moreover, the second coefficient B may be a variable which becomes, after a value is inputted from the adjuster to the automatic operation correcting means 42, the inputted value over a given period of time, or a variable which becomes, after the correction instruction value ΔP2 is inputted from the manipulator 2 to the automatic operation correcting means 42, a preset value over a given period of time. For example, in view of preventing the correction of the operation of the slave arm 1 from being sharp, the given time period may be 0.5 seconds or more, or may be 1 second or more. Further, in view of the operator acknowledging that the corrected operation of the slave arm 1 is reflected, the given time period may be within 2 seconds, within 3 seconds, or within 5 seconds.

Specifically, for example, the second coefficient B may be such a variable that a relationship between a lapsed period of time since the value is inputted from the adjuster to the automatic operation correcting means 42 or the correction instruction value ΔP2 is inputted from the manipulator 2 to the automatic operation correcting means 42 and a change amount ΔB per unit time corresponds to a linear function. Further, the second coefficient B may be such a variable that the relationship between the lapsed time period and the change amount ΔB per unit time corresponds to a high-dimensional function, such as a quadratic function or a cubic function, or it corresponds to a logarithmic function. Furthermore, the second coefficient B may be such a variable that the relationship between the lapsed time period and the change amount ΔB per unit time increases stepwise.

Thus, it is possible to prevent that when the correction instruction value ΔP2 is inputted from the manipulator 2 to the automatic operation correcting means 42, the operation of the slave arm 1 is sharply corrected and the slave arm 1 operates in an unexpected direction.

In this manner, the automatic operation correcting means 42 calculates a current value for operating the drive motor M disposed at each joint (current deviation), and the motion controller 41 outputs the current value to the slave arm 1.

Thus, in the slave arm 1, the drive motor M disposed at each joint rotates so that the angles of the first joint JT1 to the sixth joint JT6 become the target angles. Here, the rotation sensor E disposed at each joint detects the angle of the joint and feeds back the detected angle to the motion controller 41. Then, the motion controller 41 calculates the position coordinates of the slave arm 1 based on the angle of each joint inputted from the rotation sensor E.

Note that in the first embodiment, a form in which the position coordinate information is inputted as the correction instruction value ΔP2 from the manipulator 2 to the automatic operation correcting means 42 is adopted, but it is not limited to this. For example, a form in which the correction instruction value ΔP2 is the speed instruction value may be adopted, or a form in which the correction instruction value ΔP2 is the torque instruction value may be adopted.

When the correction instruction value ΔP2 is the speed instruction value, a value obtained by multiplying the speed instruction value as the correction instruction value ΔP2 by the second coefficient B (manual speed instruction value) is inputted to the subtractor 42e. Further, the subtractor 42e is supplied with a value which the position controller 42c obtains by multiplying the speed instruction value generated based on the operational instruction for the robot in the automatic operation (ΔP1; position instruction value) and a present position value, by the first coefficient A (corrected speed instruction value). Furthermore, the subtractor 42e is supplied with a present speed value generated by the differentiator 42d, from this differentiator 42d.

Then, the subtractor 42e adds the corrected speed instruction value to the inputted manual speed instruction value and generates the speed deviation based on the value obtained by subtracting the present speed value. Note that the operation after the subtractor 42e generates the speed deviation is executed in the similar manner to that described above.

Similarly, when the correction instruction value ΔP2 is the torque instruction value, a value obtained by multiplying the torque instruction value as the correction instruction value ΔP2 by the second coefficient B (manual torque instruction value) is inputted to the subtractor 42g. Further, the subtractor 42g is supplied with a value obtained by multiplying the torque instruction value generated by the speed controller 42f by the first coefficient A based on the speed deviation inputted to the speed controller 42f via the position controller 42c and the subtractor 42e in response to the operational instruction for the robot in the automatic operation (ΔP1; position instruction value) (corrected torque instruction value). Furthermore, the subtractor 42g is supplied with the present current value detected by the current sensor C.

Then, the subtractor 42g adds the corrected torque instruction value to the inputted manual torque instruction value and subtracts the present current value to generate the current deviation. The subtractor 42g sends the generated current deviation to the drive motor M to drive the drive motor M.

In the robot system 100 according to the first embodiment configured as above, the control device 4 is configured, while the slave arm 1 is operating at a speed equal to or higher than the first threshold, even when the operational instruction value for correcting the operation of the slave arm 1 is inputted from the manipulator 2 during the automatic operation of the slave arm 1, to prevent the correction of the operation of the slave arm 1.

By correcting the operation of the slave arm 1 in this manner, it is prevented that the operation of the slave arm 1 is sharply corrected and the slave arm 1 operates in the unexpected direction.

Further in the robot system according to the first embodiment, the control device 4 is configured to cause the output device 3 to output the correction preventing information when the operational instruction value for correcting the operation of the slave arm 1 is inputted from the manipulator 2 while the slave arm 1 is operating at a speed equal to or higher than the first threshold during the automatic operation of the slave arm 1.

Thus, the operator is able to understand the reason why the operation of the slave arm 1 is not corrected even though he/she manipulated the manipulator 2.

Second Embodiment

A robot system according to a second embodiment is configured so that, in the robot system according to the first embodiment, when the operational instruction value for correcting the operation of the slave arm is inputted from the manipulator during the automatic operation of the slave arm and the slave arm is operating at a speed equal to or higher than the first threshold, the control device controls the slave arm to bring the operating speed of the slave arm lower than the first threshold.

Further, in the robot system according to the second embodiment, the control device may be configured to allow the operation of the slave arm to be corrected in a case where the slave arm is operating at a speed lower than the first threshold when the operational instruction value for correcting the operation of the slave arm is inputted from the manipulator during the automatic operation of the slave arm.

Hereinafter, one example of the robot system according to the second embodiment is described with reference to FIG. 6. Note that, since the robot system according to the second embodiment has a similar configuration to the robot system according to the first embodiment, detailed description of the configuration thereof is omitted.

[Operation and Effect of Robot System]

Figure 6:
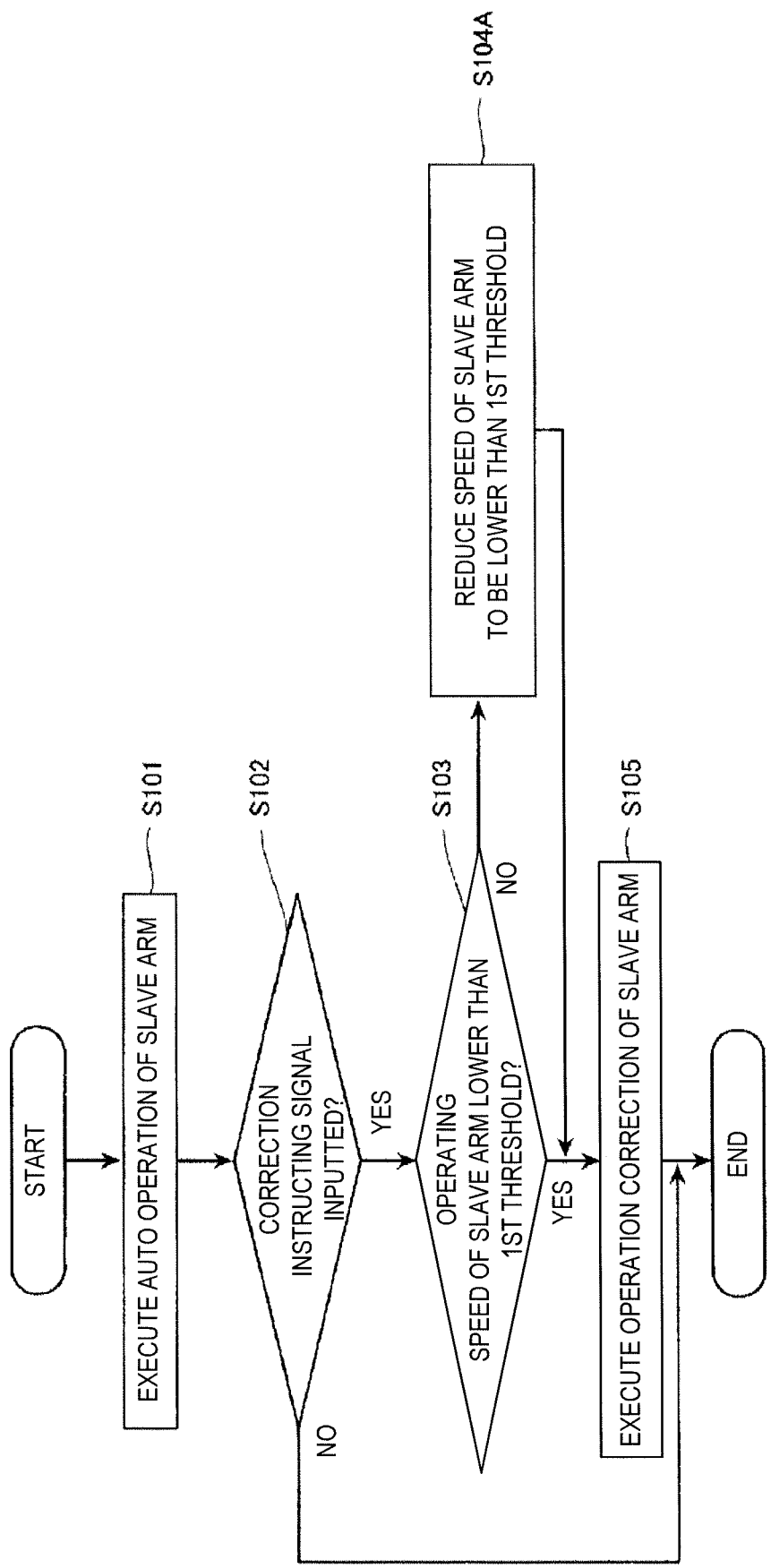
FIG. 6 is a flowchart illustrating one example of operation of a robot system according to a second embodiment.

FIG. 6 is a flowchart illustrating one example of operation of the robot system according to the second embodiment.

As illustrated in FIG. 6, although the operation of the robot system 100 according to the second embodiment is basically the same as the operation of the robot system 100 according to the first embodiment, it is different in that Step S104A is executed instead of Step S104.

Specifically, if the operating speed of the slave arm 1 is equal to or higher than the first threshold (NO at Step S103), the motion controller 41 of the control device 4 controls the slave arm 1 to bring the operating speed lower than the first threshold (Step S104A).

Then, when the operating speed of the slave arm 1 falls below the first threshold, the motion controller 41 of the control device 4 performs the operation correction of the slave arm 1 based on the correction instructing signal inputted from the manipulator 2 (Step S105) and ends this program.

Note that when the motion controller 41 of the control device 4 is controlling the slave arm 1 to bring the operating speed of the slave arm 1 lower than the first threshold, the control device 4 may cause the output device 3 to output the letter/character information of "operating speed of the arm 1 reducing etc."

Even with the robot system 100 according to the second embodiment configured as above, similar operations and effects to those of the robot system 100 according to the first embodiment are obtained.

Further in the robot system 100 according to the second embodiment, when the operational instruction value for correcting the operation of the slave arm 1 is inputted from the manipulator 2 during the automatic operation of the slave arm 1 and the slave arm 1 is operating at a speed equal to or higher than the first threshold, the control device 4 controls the slave arm 1 to bring the operating speed of the slave arm lower than the first threshold. Then, when the operating speed of the slave arm 1 falls below the first threshold, the control device 4 allows the operation of the slave arm 1 to be corrected.

Thus, even when the slave arm 1 is operating at equal to or higher than the first threshold, by the control device 4 bringing the operating speed of the slave arm 1 lower than the first threshold, the operator is able to correct the operation of the slave arm 1.

It is apparent for a person skilled in the art that many improvements or other embodiments of the present disclosure are possible from the above description. Therefore, the above description is to be interpreted only as illustration, and it is provided in order to teach a person skilled in the art the best mode in which the present disclosure is implemented. Details of the structures and/or functions of the present disclosure may be substantially changed without departing from the spirit of the present disclosure.

INDUSTRIAL APPLICABILITY

Since the robot system of the present disclosure and the method of operating the same are capable of preventing that, when correcting the operation of the robot during the automatic operation of the robot, the operation of the robot is corrected sharply and the robot operates in the unexpected direction, they are useful in the field of industrial robots.

DESCRIPTION OF REFERENCE CHARACTERS

1 Slave Arm
2 Manipulator
3 Output Device
4 Control Device
5 Storage Device
11a First Link
11b Second Link
11c Third Link
11d Fourth Link
11e Fifth Link
11f Sixth Link
24
12 End Effector
15 Pedestal
40 Receiver
41 Motion Controller
42 Automatic Operation Correcting Means
42a Adder
42b Substractor
42c Position Controller
42d Differentiator
42e Subtractor
42f Control Device
42g Subtractor
43 Output Controller
51 Task Program
52 Operation Sequence Information

The invention claimed is:

1. A robot system comprising:
a manipulator configured to receive a manipulating instruction from an operator;
a slave arm having a plurality of joints; and
a storage device storing a task program; and
a control device configured to control operation of the slave arm, wherein:
when the slave arm is operating at a speed equal to or higher than a first predetermined threshold and when a correction instruction value to correct the operation of the slave arm is inputted from the manipulator during an automatic operation of the slave arm, the control device is configured to prevent the correction of the operation of the slave arm and continue the automatic operation of the slave arm,
when the slave arm is operating at a speed lower than the first predetermined threshold and when the correction instruction value to correct the operation of the slave arm is inputted from the manipulator during the automatic operation of the slave arm, the control device is configured to allow the correction of the operation of the slave arm, and
the control device is configured to add the correction instruction value to an operational instruction value, which is based on automatic operation information acquired from the task program, and perform the correction of the operation of the slave arm as a function of a sum of the correction instruction value and the operational instruction value.

2. The robot system of claim 1, further comprising an output device,
wherein when the correction instruction value to correct the operation of the slave arm is inputted from the manipulator and when the slave arm is operating at a speed equal to or higher than the first predetermined threshold during the automatic operation of the slave arm, the control device is configured to cause the output device to output correction preventing information indicating that the correction of the operation of the slave arm is prevented.

3. The robot system of claim 1, wherein when the correction instruction value to correct the operation of the slave arm is inputted from the manipulator during the automatic operation of the slave arm and the slave arm is operating at a speed equal to or higher than the first predetermined threshold, the control device is configured to control the slave arm to decrease the operating speed of the slave arm to be lower than the first predetermined threshold.

4. A method of operating a robot system including a manipulator configured to receive a manipulating instruction from an operator, a slave arm having a plurality of joints, and a storage device storing a task program, the method comprising:
causing the manipulator to output a correction instruction value to correct operation of the slave arm when the slave arm is under an automatic operation;
preventing the correction of the operation of the slave arm and continuing the automatic operation of the slave arm when the slave arm is operating at a speed equal to or higher than a first predetermined threshold;
allowing correction of the operation of the slave arm when the slave arm is operating at a speed lower than the first predetermined threshold;
adding the correction instruction value to an operational instruction value, which is based on automatic operation information acquired from the task program; and
performing the correction of the operation of the slave arm as a function of a sum of the correction instruction value and the operational instruction value.

5. The method of operating the robot system of claim 4, wherein:
the robot system further includes an output device, and
the method further comprises causing the output device to output correction preventing information indicating that the correction of the operation of the slave arm is prevented.

6. The method of operating the robot system of claim 4, further comprising causing the slave arm to operate at a speed lower than the first predetermined threshold when the slave arm is operating at a speed equal to or higher than the first predetermined threshold.

* * * * *